(12) United States Patent
Oberstar et al.

(10) Patent No.: US 11,980,735 B2
(45) Date of Patent: May 14, 2024

(54) DYNAMIC AGENT INJECTION FOR CARDIOVASCULAR CHARACTERIZATION

(71) Applicant: Wisconsin Alumni Research Foundation, Madison, WI (US)

(72) Inventors: Erick Louis Oberstar, Verona, WI (US); Michael Antonio Speidel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 756 days.

(21) Appl. No.: 16/534,725

(22) Filed: Aug. 7, 2019

(65) Prior Publication Data
US 2021/0322668 A1 Oct. 21, 2021

(51) Int. Cl.
| | | |
|---|---|---|
| *A61M 5/00* | (2006.01) | |
| *A61B 5/026* | (2006.01) | |
| *A61B 5/0275* | (2006.01) | |
| *A61B 6/00* | (2006.01) | |
| *A61B 6/03* | (2006.01) | |

(Continued)

(52) U.S. Cl.
CPC ............ *A61M 5/007* (2013.01); *A61B 6/481* (2013.01); *A61B 6/507* (2013.01); *A61M 5/1408* (2013.01); *A61M 5/1452* (2013.01); *A61B 5/0263* (2013.01); *A61B 5/0275* (2013.01); *A61B 6/032* (2013.01); *A61B 8/06* (2013.01);
(Continued)

(58) Field of Classification Search
CPC .. A61M 5/007; A61M 5/1408; A61M 5/1452; A61M 2205/3334; A61M 2230/04; A61B 6/481; A61B 6/507; A61B 5/0263; A61B 5/0275; A61B 6/032; A61B 8/06; A61B 8/481; A61B 5/021; A61B 5/7285; A61B 6/504; A61B 6/541

See application file for complete search history.

(56) References Cited

U.S. PATENT DOCUMENTS 9,233,176 B2 * 1/2016 Lawaczek .......... A61K 49/0452
9,642,964 B2   5/2017 Neukirchen et al.
(Continued)

FOREIGN PATENT DOCUMENTS

CN         104159516 A  * 11/2014  ............. A61B 6/025

OTHER PUBLICATIONS

Albert et al. 1993 MRM 29:700-708 (Year: 1993).*
(Continued)

*Primary Examiner* — Keith M Raymond
*Assistant Examiner* — Patrick M Mehl
(74) *Attorney, Agent, or Firm* — Crawford Maunu PLLC (57) ABSTRACT

Aspects of the disclosure are directed to methods and/or apparatuses involving modifying flow and/or concentration of an agent being injected for characterizing a vascular system. As may be implemented in accordance with one or more embodiments, a liquid including an agent is injected into a vascular system, by dynamically modulating a flow rate of the agent being injected over a range of flow rates. The vascular system is characterized based on a response of the vascular system to the dynamic modulation. In some implementations, such an approach involves using an injector that operates to separately control the rate at which an agent and other liquid such as saline are injected. These approaches can be implemented with modulation schemes using one or more of a variety of functions.

20 Claims, 5 Drawing Sheets

(51) Int. Cl.
  *A61B 6/50* (2024.01)
  *A61B 8/06* (2006.01)
  *A61B 8/08* (2006.01)
  *A61M 5/14* (2006.01)
  *A61M 5/145* (2006.01)

(52) U.S. Cl.
  CPC ...... *A61B 8/481* (2013.01); *A61M 2205/3334* (2013.01); *A61M 2230/04* (2013.01)

(56) References Cited

U.S. PATENT DOCUMENTS

| | | | |
|---|---|---|---|
| 9,858,387 B2 | 1/2018 | Lavi et al. | |
| 2015/0025370 A1* | 1/2015 | Neukirchen | A61B 6/504 600/432 |
| 2015/0209515 A1* | 7/2015 | Houde | A61M 5/19 600/432 |
| 2016/0106916 A1* | 4/2016 | Burmaster | A61M 5/1413 604/28 |
| 2016/0278725 A1* | 9/2016 | Van Nijnatten | A61B 6/461 |
| 2020/0022664 A1* | 1/2020 | Moore | G06T 7/0016 |

OTHER PUBLICATIONS

Wu et al. 2018 Am. J. Neuroradiol. 39:1871-1877 (Year: 2018).*
Bögel et al., "Robust Blood Flow Velocity Estimation from 3D Rotational Angiography," Conference: IEEE International Conference on Image Processing (ICIP), Athens, Greece, p. 5 (Sep. 2018).
Catanho et al., "Model of Aortic Blood Flow Using the Windkessel Effect," University of California of San Diego, San Diego, CA (Oct. 15, 2012).
Elad et al., "Physical and Flow Properties of Blood," Standard Handbook of Biomedical Eng. and Design; 3:3.1-3.25, 2004.
Keller et al., "Noninvasive measurement of velocity profiles and blood flow in the common carotid artery by pulsed Doppler ultrasound," Stroke; 7(4):370-377 (Jul.-Aug. 1976).
Lacroix, 3D Optical flow analysis of a pulsed contrast agent in the bloodstream. Application to virtual angiography and Magnetic Particle Imaging.
Likittanasombut et al., "Volume Flow Rate of Common Carotid Artery Measured by Doppler Method and Color Velocity Imaging Quantification (CVI-Q)," J of Neuroimaging; 16(1):34-38, (Feb. 2006).
Shaughnessy et al., "Quantitative flow and velocity measurements of pulsatile blood flow with 4D-DSA," Proceedings of the SPIE, vol. 10132, id 10325R pp. 1 (Mar. 1, 2017).
Shaughnessy et al., "Measuring Blood Velocity Using 4D DSA: a Feasibility Study," Medical Physics; 45(10) (Aug. 2018).
Wu et al., "Quantification of Blood Velocity with 4D Digital Subtraction Angiography Using the Shifted Least-Squares Method," American J of Neuroradiology; pp. 1-7 (Sep. 13, 2018).
Yousem et al., "Injection rates for neuroangiography: results of a survey," American J of Neuroradiology; 22(10):1838-1840 (Nov./Dec. 2001).

* cited by examiner

DYNAMIC AGENT INJECTION FOR CARDIOVASCULAR CHARACTERIZATION

STATEMENT REGARDING FEDERALLY SPONSORED RESEARCH AND DEVELOPMENT

This invention was made with government support under HL116567 awarded by the National Institutes of Health. The government has certain rights in the invention.

OVERVIEW

Aspects of the present disclosure are directed to characterization of a cardiovascular system via the dynamic injection of an agent.

Various aspects of the disclosure address challenges relating to cardiovascular characterization. For instance, it can be challenging to utilize an injected agent at locations distal to an injection site, and in particular, at distal locations of the cardiovascular system in which pulsatile flow diminishes as may be due to diffusion processes and fluid dynamics. In addition, injection may take place in regions of strong flow variation, in order to obtain a desired response.

These and other matters have presented challenges to the characterization of cardiovascular flow and/or of a cardiovascular system, for a variety of applications.

SUMMARY

Various example embodiments are directed to apparatuses and methods, which may address various challenges including those noted above.

As may be implemented in accordance with one or more embodiments, the flow rate and/or concentration of an agent or agents injected into a cardiovascular system are temporally varied, and the cardiovascular system is characterized using the temporal variations. Such an approach may involve modulating one or both of agent flow rate and agent concentration at an injection site, and detecting characteristics of the modulation at a location distal to the injection site. These approaches can provide stronger contrast pulsatility in distal portions of a vascular network, thereby enabling flow quantification in distal vessels. Accordingly, characterization of various aspects of the cardiovascular system is facilitated, such as by ascertaining one of more of pressure, flow, and compliance.

Further aspects of the present disclosure are directed to a method as follows. A liquid including an agent is injected into a vascular system, by dynamically modulating a flow rate (as also applicable to concentration) of the agent being injected over a range of flow rates. The vascular system is characterized based on a response of the vascular system to the dynamic modulation.

Another embodiment is directed to an apparatus comprising an injector and an actuation controller. The injector is configured and arranged to inject a liquid including an agent into a vascular system. The actuation controller (including circuitry) is configured and arranged to control the injector for dynamically modulating a flow rate of the agent being injected over a range of flow rates, therein providing characterization of the vascular system based on a response of the vascular system to the dynamic modulation. The actuation controller may thus execute algorithms to generate functions for driving the dynamic modulation.

The above discussion/summary is not intended to describe each embodiment or every implementation of the present disclosure. The figures and detailed description that follow also exemplify various embodiments.

BRIEF DESCRIPTION OF FIGURES

Various example embodiments may be more completely understood in consideration of the following detailed description and in connection with the accompanying drawings, in which:

FIGS. 3-5 show exemplary plots for respective concentrations of an Iohexol agent, as may be utilized in accordance with one or more embodiments, in which:

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as may be used throughout this application is by way of illustration, and not limitation.

DETAILED DESCRIPTION

Aspects of the present disclosure are believed to be applicable to a variety of different types of apparatuses, systems and methods involving the characterization of a cardiovascular system via injection of an agent. Various aspects of the present disclosure have been shown to be beneficial when used in the context of generating modulations involving dynamically modulating one or both of agent flow rate and concentration at an injection site, and monitoring the modulations in distal regions of the vascular system. Arbitrary, periodic or other time varying concentrations of contrast agent can thus be obtained. In certain embodiments, such approaches involve utilizing a two-stage injection mode in which the agent is injected in a liquid including other fluid, such that one or both of the volume of the injected liquid (including the agent) and the concentration of the agent within that volume may be modulated. In the context of various embodiments, it has been recognized/discovered that these approaches can facilitate detection of variations in the resulting flow through the vascular system, which is influenced by the vascular system. Various methods and apparatuses may be implemented to achieve these embodiments. In this manner, challenges to characterizing vascular systems such as those discussed above may be addressed.

A variety of different characterizations may be made for vascular systems, in accordance with embodiments herein. For instance, blood flow quantification can be achieved before and after the treatment of vascular disease. In the setting of x-ray guided interventional procedures, an x-ray system may be used to image an injected agent, such as an iodinated contrast agent, as it flows through the treated vasculature. Variations in flow and/or concentration of the injected agent can be imaged and used to characterize the vasculature. Other types of imaging may involve use of ultrasound, magnetic resonance, or computed tomography. In certain implementations, pressure variations, downstream and/or upstream from an injection site, may be utilized to characterized the vasculature. These and other approaches as characterized herein may be utilized with two-dimensional (2D) digital subtraction angiography (2D DSA), four-dimensional (4D) DSA, or pulsatile contrast analysis, using modulation to facilitate data consistency and mitigate artifacts.

As may be implemented in accordance with one or more embodiments, a power injection apparatus and method involve purposefully introducing temporal variations in flow rate and/or concentration of a contrast agent. This approach may be used to maintain stronger contrast pulsatility in the distal portions of a vascular network, thereby enabling flow quantification in distal vessels. When mixed with fluid prior to injection, the concentration of the contrast agent can be varied by increasing or decreasing its flow rate, and/or by increasing or decreasing the flow rate of fluid with which the contrast agent is mixed. These approaches facilitate varying the rate of injection over time according to a variety of modulation schemes, as may include sinusoidal, square, triangle, swept sine, white noise, aperiodic, or other user-programmable profiles. Accordingly, specific and different periods of oscillation, peak and mean amplitudes, phase, and frequency can be utilized with dynamic modulation. For instance, contrast agent injection may be purposefully modulated at a frequency lower than the cardiac rate in order to improve contrast pulsatility in distal vasculature and enable more reliable DSA-based flow quantification. Further, one or more of these modulation schemes may be implemented with a bias, for example where flow rate is varied between high and low values around a bias level of flow rate, the low value is a zero or positive value.

As utilized herein, the term dynamically modulating refers to modulation that is dynamically changed during the application of the modulation. For example, a flow rate of agent may be modulated between respective values at a particular frequency. Dynamically modulating such a flow rate of agent involves changing the frequency at which the flow rate is modulated, such as by implementing a frequency sweep, during the modulation. Accordingly, dynamic modulation does not refer to a modulation that is static, such as by maintaining a frequency at which modulation is effected.

In some implementations, a dual-barrel power injector may be used to respectively inject agent and other fluid such as saline via each of the barrels, with the two being mixed prior to and/or during injection. The dual-barrel power injector may include plunger actuators or other fluid delivery components (e.g., gears, pumps) that are independently controlled. For general information regarding injecting agents, and for specific information regarding mechanisms for injection that may be utilized in connection with one or more embodiments, a syringeless injector may be implemented with the CT Exprès injector, available from Bracco Injeneering S. A., Lausanne, Switzerland). As such, both concentration vs. time and total flow vs. time can be modulated. By controlling the injector barrels independently, specific and different periods of oscillation, peak and mean amplitudes can be defined. In this context, the injector barrels may be controlled together in a manner similar to single barrel injectors relative to pressures and other conditions that facilitate safe use with humans.

Consistent with the above, certain embodiments involve characterizing a cardiovascular system using force and/or pressure measurements. For instance, backpressure may be measured upstream from an injection cite, as may be caused by injecting into a blood vessel with cardiac flow. Such backpressure may induce back force of 0.037 lbf per mmHg of pressure for a fluid system. This corresponds with a ~0.19 lbf force for a 5 mmHg change in pressure. For lower concentrations of a contrast agent such as Iohexol (or contrast with similar viscosity), 12-bit (or higher) force resolutions can be used to measure pressure changes on the order of 5 mmHg (or better), facilitating intra-arterial pressure measurements from an injector itself. Higher resolution than 12 bit may be utilized for higher viscosity contrast agents.

In certain embodiments, disturbance forces are detected as an acceleration to motion control, noting that Force=Mass*Acceleration. This acceleration alters the velocity trajectory as an acceleration disturbance into the system that can be detected by velocity measurement with an appropriately sampled high-resolution encoder (e.g., higher than 5000 lines per revolution quadrature decoded [20,000 increments per revolution], such as when utilizing the gearbox depicted in FIG. 1).

In other embodiments, pressure is monitored with pressure transducers in line with a fluid system at the outlet of a syringe or the outlet of a tube into a catheter. Both locations facilitate measurement points of the disturbance pressure from the cardiovascular system. Pressure sensitivity may be set to suit particular embodiments. For instance, where approximately 85% of the pressure drop is across the catheter, a pressure sensitivity 1 mmHg over the range of system pressures utilizes a 14-bit or higher resolution on a pressure transducer at the tube/catheter interface.

Various aspects of the present disclosure are directed to a method in which a flow rate of agent being injected into a vascular system (e.g., along with saline) is dynamically modulating over a range of flow rates, and the vascular system is characterized based on its response to the dynamic modulation. Modulating the flow rate of the agent may involve one or more of a variety of types of modulation, which may result in a different concentration of the agent being injected, a different amount of the agent being injected and/or a different amount of overall liquid including the agent being injected. In some implementations, the concentration of the agent mixed with a constant flow of other fluid such as saline is modulated. In other implementations, the concentration of the agent in liquid is maintained while modulating the total volume of the liquid. In yet other implementations, the actual flow rate of the agent is unchanged while the relative flow rate of the agent to the liquid in which it is injected is modified by modifying the actual flow rate of the liquid.

The vascular system may be characterized in one or more of a variety of manners. For instance, the vascular system may be imaged, or pressure variations in the vascular system may be detected, based on the dynamic modulation. In some embodiments, the agent is imaged in the vascular system and the resulting images are used to detect differences in modulation characteristics of the agent at a remote portion of the vascular system, relative to modulation characteristics of the agent at an injection site at which the liquid is injected into the vascular system. This may involve, for example, using the modulation to characterize portions of the vascular system at which pulsatile flow has diminished.

Consistent with the above-noted discussion, it has been recognized/discovered that utilizing dynamic modulation, such as by applying a frequency sweep to injected agent flow rate or concentration, enhances the ability to detect related changes in the agent at such distal locations. In many contexts, this approach imparts data such as a signature to volumes of vascular fluid at an injection site, which can then be recognized at distal locations.

In various contexts, the remote or distal area at which the vascular system is characterized may be either upstream or downstream relative to the injection site. For instance, in applications such as embolization of vasculature in the liver, reflux of contrast agent may be used to determine when the procedure is complete. The reflux may involve a periodic upstream flow.

The dynamic modulation is carried out using a variety of approaches, to suit particular applications. For instance, one or more of flow rate of the agent, concentration of the agent, and flow rate of the liquid may be modulated. Such modulation may include modulating between high and low values respectively above and below an offset value, such that a low rate still involves a positive rate (e.g., so as not to encompass an effective a negative flow or concentration). The modulation may involve pseudoperiodic, periodic, aperiodic or arbitrary modulation, or may involve bolus shaping. Various functions may be implemented for the modulation, such as by using a waveform including one or more of a sinusoidal waveform, a swept sinusoidal waveform, a triangle waveform, a square waveform, an arbitrary waveform, and a combination thereof. Frequency may be modulated (e.g., using a frequency sweep), amplitude (e.g., concentration or volume) may be modulated, or a phase of a waveform may be shifted. Higher order modulation schemes may also be utilized, such as those involving the superposition of multiple frequency waveforms together.

In some embodiments, the flow rate of the agent is modulated using cardiovascular flow of blood in the vascular system to modulate the concentration of the agent flowing through the system. Changes in the concentration of the agent are detected at a remote portion of the cardiovascular system, relative to a portion of the vascular system at which the liquid is injected.

In a more particular embodiment, cardiovascular flow of blood in the vascular system is used as a carrier signal, and data is coded onto the cardiovascular flow by modulating a frequency, phase or amplitude characteristic of the concentration of the agent injected via the liquid. For instance, amplitude may be varied between maximum and minimum flow rates, with the minimum being at or above zero. The vascular system is then characterized by detecting changes in the data coded onto the cardiovascular flow as the blood flows through the vascular system.

Another embodiment is directed to an ECG gating approach. In this context, the flow rate (e.g., volume and/or concentration) of agent in the liquid can be modulated for generating contrast flows of the agent that are synchronized with the cardiac cycle of the vascular system. For instance, the modulation may synchronize to a systolic or diastolic period of the cardiac cycle. As such, ECG gating can be effected, in which a phase relationship of modulation of the agent is synchronized with the cardiac cycle.

A particular use-case scenario involves utilizing short duration contrast pulsation for imaging aneurysms, in which stream lines and jets inside and entering into the aneurysm may be monitored as well. For instance, low duty cycle square waves can be utilized for the modulation at a specific frequency.

Another embodiment is directed to an apparatus comprising an injector and an actuation controller. The injector is configured and arranged to inject a liquid including an agent into a vascular system. The actuation controller (including circuitry) is configured and arranged to control the injector for dynamically modulating a flow rate of the agent being injected over a range of flow rates, therein providing characterization of the vascular system based on a response of the vascular system to the dynamic modulation. This approach may involve, for example, computer circuitry that executes software or an algorithm to carry out desired functionality. In some implementations, the injector includes a dual barrel injector, each barrel having a plunger that is independently controlled by the actuation controller, relative to the plunger in the other barrel. In this context, the agent can be introduced using one of the barrels, and a liquid such as saline can be introduced using the other one of the barrels. The relative flow rates can be independently controlled, which facilitates dynamically (e.g., continuously) modulating one or both of the concentration of the agent and flow of the combined liquid. For instance, the actuation controller may operate the injector for dynamically modulating the flow rate by modulating one or both of the concentration and volume of the agent being injected. Dynamically modulating the flow rate may include, for example, modulating a flow rate (actual or relative) of the agent between high and low values respectively above and below an offset value and in accordance with a waveform.

The actuation controller may be implemented in a variety of manners. In some embodiments, the actuation controller includes circuitry programmed to modulate the actuation of respective fluid supplies of the agent and liquid in which the agent is mixed, such as by actuating respective plungers, to dynamically modulate the flow rate of the agent as it is injected into the vascular system.

In some embodiments, the apparatus includes componentry for assessing a response of the vascular system. For instance, certain embodiments involve imaging circuitry that images the agent in the vascular system. The images are used to provide an indication the effect of the vascular system upon the dynamic modulation and therein characterizing the vascular system. Other embodiments may employ sensors, such as force sensors, to assess response of the vascular system.

In a more particular embodiment, the apparatus uses an ECG signal from the vascular system (from a patient) as an input for controlling the modulation. For instance, the actuation controller may dynamically modulate the flow rate based on the ECG signal from the vascular system. This may, for example, involve synchronizing the dynamic modulation to the ECG signal.

Figure 1:
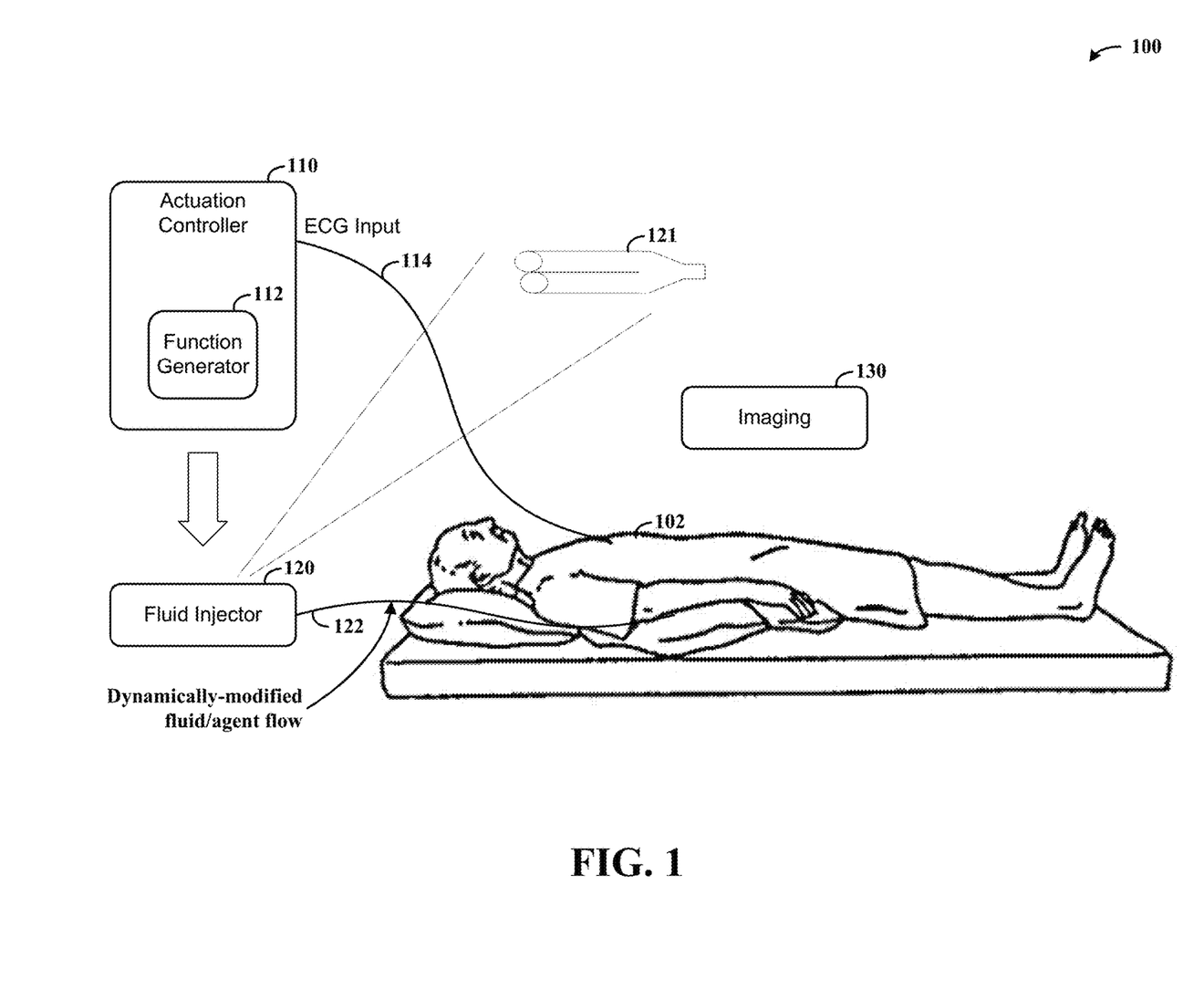
FIG. 1 shows an apparatus and related method for assessing a vascular system in a human patient, as may be implemented in accordance with various embodiments.

Turning now to the figures, FIG. 1 shows an apparatus 100 and related method for assessing a vascular system in a human patient 102, as may be implemented in accordance with one or more embodiments. The apparatus includes an actuation controller 110 and a fluid injector 120 that operate together to inject an agent into the patient's vascular system utilizing a dynamically modified flow rate, consistent with one or more embodiments herein. By way of example, a dual-barrel component 121 is shown, which may be implemented in fluid injector 120 for injecting fluid such as saline and an agent at respective flow rates (and resulting concentration). A catheter 122 (with a lead tube) couples fluid from the fluid injector 120 to the patient 102, shown arbitrarily positioned. The actuation controller 110 may include, for example, a function generator 112 that generates a dynamic output such as a waveform, which controls the fluid injector 120 for injecting an agent using dynamic flow and/or concentration characteristics.

The dynamically injected agent can then be utilized to characterize the vascular system of the patient 102 in a variety of manners. In some implementations, the fluid injector 120 includes pressure or other force sensing componentry that detects pressure or force response of the vascular system. Additional sensors may be implemented with the patient in this regard, such as shown with FIG. 2 and discussed blow. In certain implementations, the apparatus 100 includes imaging component 130, which includes components, related circuitry and control instructions for imaging the vascular system of the patient 102, including variations in the agent at regions of the vascular system that are distal to an injection site.

A variety of configurations of the actuation controller 110 and injector 120 are implemented to facilitate desired system dynamics, in accordance with various embodiments. For instance, a controlled actuator (with decoupled electromechanical dynamics) may utilize a bandwidth of 15-100 Hz to cover an anticipated range of vascular impedance dynamics. Electromechanical properties of the system as well as dynamics imparted on the flow by the fluid system from a syringe through a catheter (and, e.g., filtration effects) may be modelled and utilized in determining a proper modulation scheme. The actuation controller 110 may decouple reflected characteristics such as mass/inertia, hydraulic resistance, and compliance, in order to facilitate responsiveness of the related agent modulation.

For instance, a state feedback controller can be used with a load observer to obtain estimates of fluid dynamic effects of the system, which could be compensated for and leveraged to estimate the cardiac pressure/flow inducing a disturbance into the controlled contrast flow. A nested loop state feedback system with command feed forward may also be utilized, and may further include integrated position control (integrated flow control). For instance, a feed forward controller may generate the majority of manipulation applied to for actuation, and any disturbances can compensated for by a closed loop controller, thereby providing an estimate of disturbance inputs (force/pressure/flow) from an additional flow sources such as a patient's heart. Controllers may be closed looped and operate at rates from 30 Hz and up to over a 50 kHz as a computational throughput requirement, and can be broken into a multi-rate control system with different loops closed at rates appropriate for the bandwidth of the particular loop.

Trajectory information, such as flow, velocity and/or position, can be input by a user and/or received via communications, for controlling the actuation controller 110 and injector 120. This may involve utilizing limits and/or ranges to achieve safe flow parameters. In some implementations, trajectories (either parameters or entire trajectories) are loaded from nonvolatile storage accessible by and/or within the actuation controller 110.

In a more particular embodiment, the apparatus uses an ECG signal, obtained from a led 114 coupled to the patient 102, as an input for controlling the modulation. For instance, the actuation controller 110 may control the fluid injector 120 to dynamically modulate the flow rate based on the ECG signal. In some implementations, the actuation controller 110 synchronizes the dynamic modulation to the ECG signal.

Figure 2:
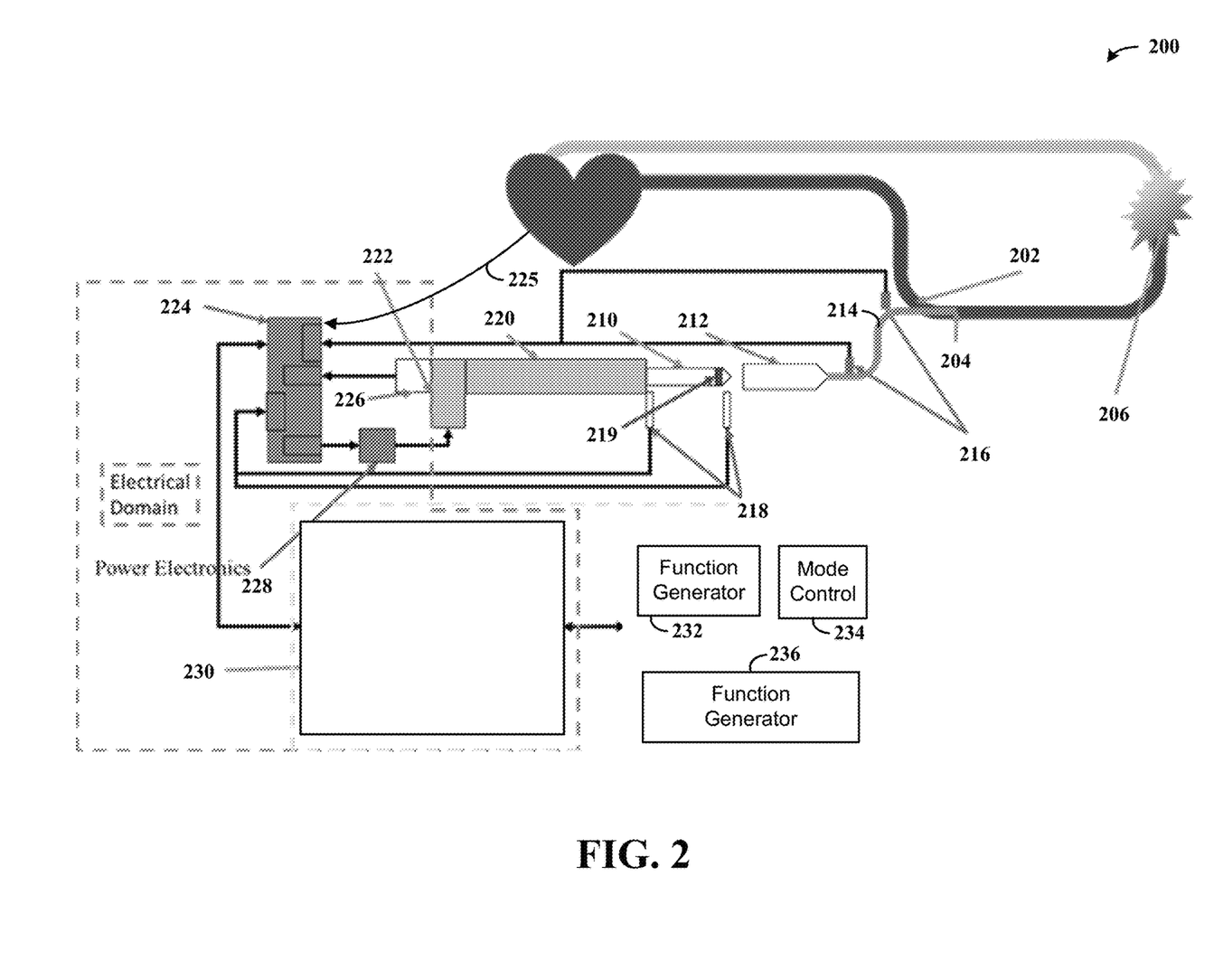
FIG. 2 shows an apparatus, as may be implemented in accordance with another embodiment.

FIG. 2 shows an apparatus 200, as may be implemented in accordance with another embodiment. The apparatus 200 includes injection components including plungers 210, a syringe barrel(s) 212 and catheter 214, shown introduced into an artery or vein 202 by way of example, at an injection site 204. Modulated fluid injected therein is utilized to assess characteristics of the vascular system including the artery or vein 202, such as at a downstream capillary bed 206 that may exhibit low pulsatile flow. Pressure transducers 216 may be utilized to monitor pressure at the points shown in the catheter 214, and a force transducer 219 may be used to detect forces at the end of the plunger.

Actuator componentry may include an actuator 220 such as a ball/screw lead driven by a gearbox and motor 222, which may be controlled via signals received at input/output (I/O) electronics 224, with feedback provided by an encoder 226. Other inputs to the I/O electronics 224 may include an ECG lead 225, which provides an ECG that may be used, for example, to synchronize the modulation to the cardiac cycle. Power electronics 228 may further interact between the I/O electronics 224 and the gear box/motor 222. Further, limit switches 218 may be used to detect positions of plungers in the syringe barrel(s)

A computer controller 230 (including computing circuitry) operates using a function generator 232 to generate a function by which injected agent is to be modulated. The computer controller may also operate using a mode controller 234, such as to control a type of injection and related operation, and a further function generator 236 (e.g., where two different functions are used to control different circuit components. In this context, the computer controller 230 along with the I/O electronics 224, encoder 226 and power electronics 228 may operate in the electrical domain, with the function and mode components 232, 234 and 236 operating therewith. For instance, the function generator 232 may be implemented to generate a sine wave with a modulated frequency, which is used by the computer controller 230 to generate an output that controls actuation of the plunger(s) 210 for injecting a fluid at a variable sinusoidal rate.

In some implementations, the apparatus 200 is operates as follows. A syringe 212 filled with a fixed iodine concentration can be modulated or a fixed flow rate of fixed concentration iodine can be modulated by the additional injection of a modulated diluting agent such as saline. A user interface coupled via computer controller 230 that may facilitate the implementation of constant, sinusoidal, swept sine, white noise, square wave/duty cycle and simulated cardiac flow waveforms with user defined amplitudes, frequencies, and delays. Further, a window function such as Boxcar, Hamming, or Hanning may be applied to the waveform to help shape frequency domain characteristics. Actuators used in this context may generate forces that, when applied to a 40 mm diameter 150 mL syringe, flows in a clinically relevant range of 0 to 9.4 mL/Sec out of each syringe.

Figure 3:
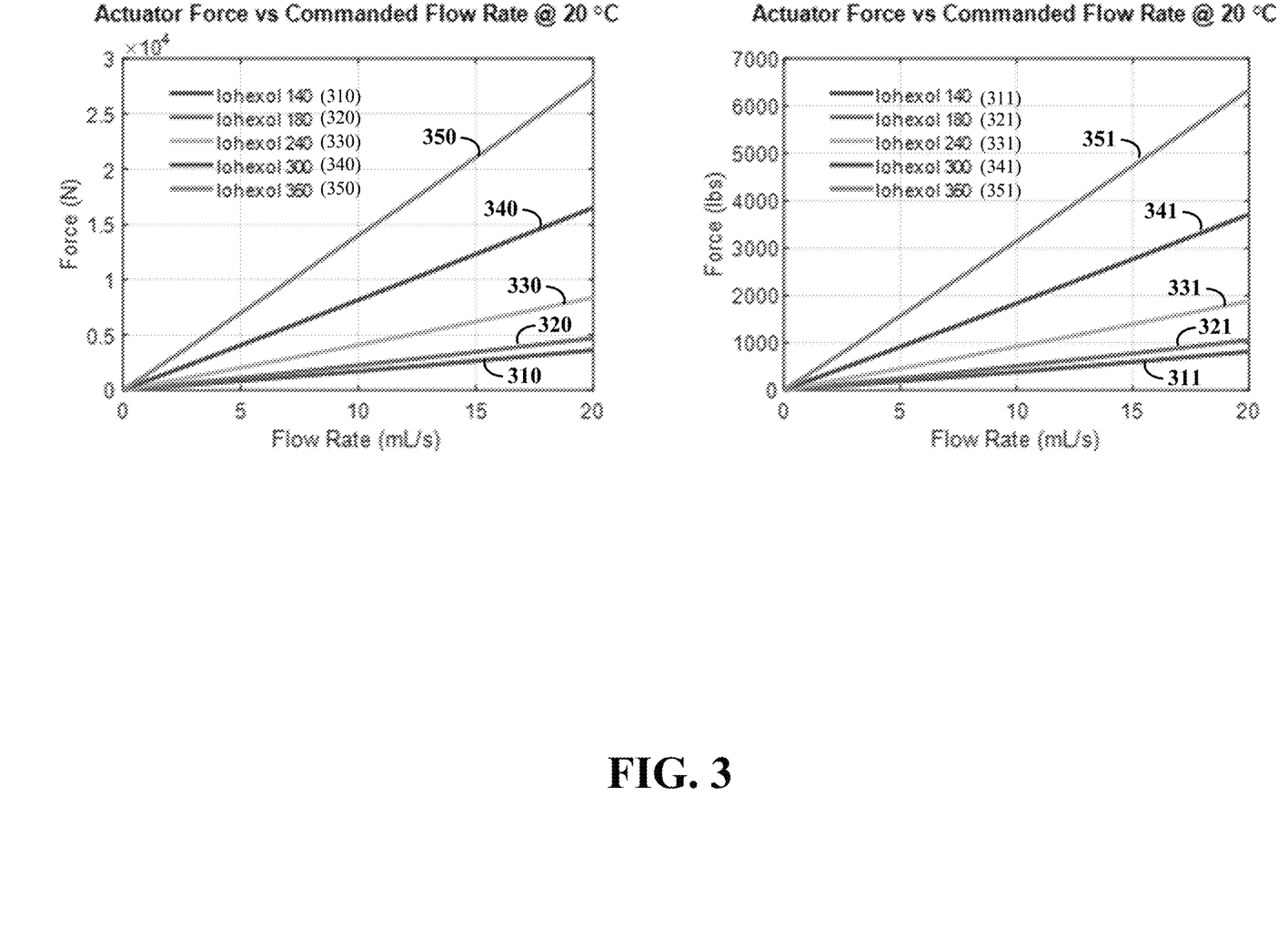
FIG. 3 shows plots depicting example actuator force respectively in newtons and pounds relative to flow rate.
Figure 4:
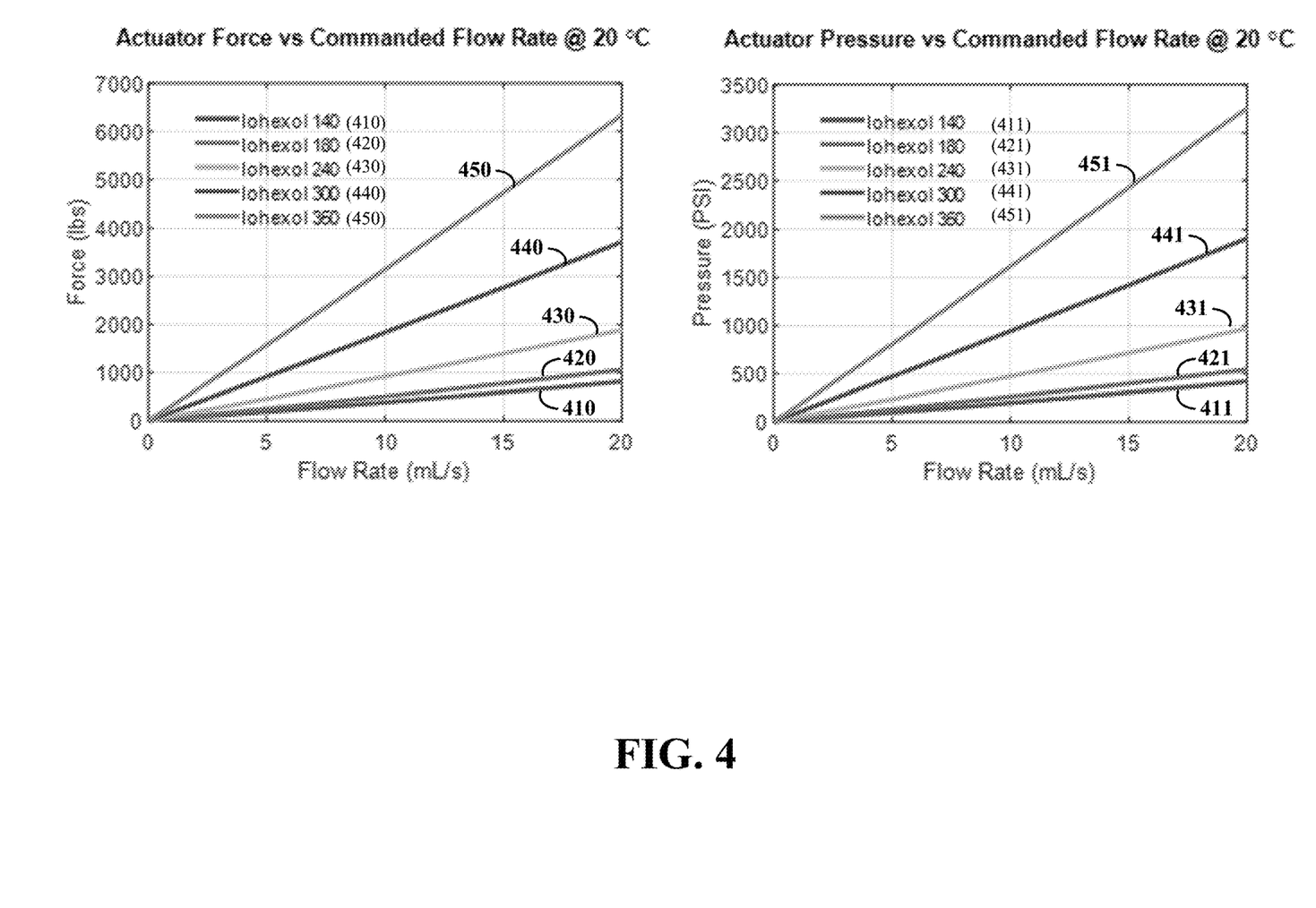
FIG. 4 shows plots respectively depicting actuator force in pounds and pressure (PSI)
Figure 5:
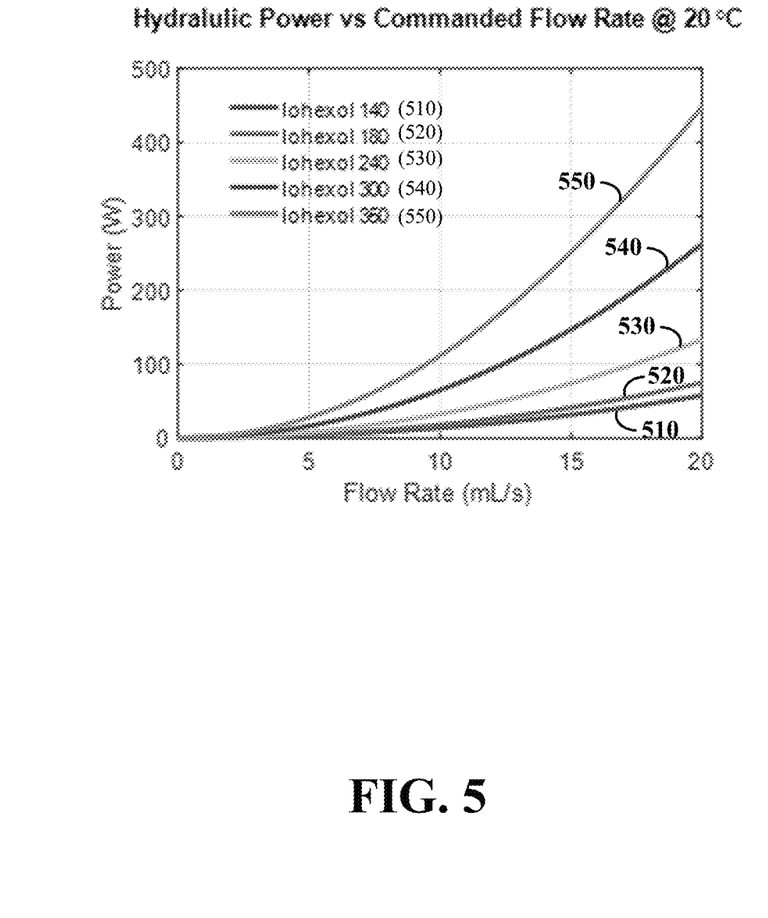
FIG. 5 shows plots of hydraulic power relative to flow rate.

FIGS. 3-5 show exemplary plots for respective concentrations of an Iohexol agent, as may be utilized in accordance with one or more embodiments. Such approaches may be implemented with a nominal fluid load (e.g., with a 40 mm diameter syringe, 1.8 mm diameter tubing to a catheter, and a 1 mm diameter catheter). The plots are exemplary, and may be scaled accordingly to the relative diameter of each of the fluid domains.

For instance, FIG. 3 shows plots 310-350, and 311-351, depicting example actuator force respectively in newtons and pounds relative to flow rate, for Iohexol at respective concentrations (mgI/ml) as noted. FIG. 4 shows plots 410-450, and 411-451, respectively depicting actuator force in pounds and pressure (PSI) for Iohexol at the same concentrations as depicted in FIG. 4.

FIG. 5 shows plots 510-550 of hydraulic power relative to flow rate, for the same Iohexol concentrations as depicted therein. Instantaneous fluid power (Pwr) may be computed by multiplying Pressure*Volume Flow Rate, and implemented as follows.

$$Pwr(W) = P*Q = P(\text{kPa})*\frac{1000 \text{ Pa}}{\text{kPa}}*Q\left(\frac{\text{cm}^3}{\text{s}}\right)*\frac{1 \text{ m}^3}{1 \times 10^6 \text{ cm}^3}$$

Power is nonlinear with flow rate, and for high bandwidth flow rates a high bandwidth power supply can be used to meet dynamic instantaneous power demands.

Based upon the above discussion and illustrations, those skilled in the art will readily recognize that various modifications and changes may be made to the various embodiments without strictly following the exemplary embodiments and applications illustrated and described herein. For example, where flow rate of an agent is modulated, such modulation may involve a relative flow rate in comparison to an accompanying fluid being injected, such as saline. In this context, the actual flow of agent may be maintained at a steady state while modulating saline with which the agent is being mixed, resulting in modulation of both agent concentration and total flow of fluid being injected. Further, different mechanisms maybe utilized to achieve desired fluid modulation, such as plungers, pumps, metered gears, screw gears, and other types of actuators. Such modifications do not depart from the true spirit and scope of various aspects of the invention, including aspects set forth in the claims.

What is claimed is:

1. A method comprising:
continuously injecting a liquid including an agent and another liquid into a vascular system, including dynamically modulating a flow rate of the agent within the liquid prior to the liquid being injected into the vascular system, relative to the other liquid, over a range of flow rates and therein causing the vascular system to exhibit a dynamic response to the dynamic modulation; and
characterizing the vascular system based on a time-varying characteristic of the dynamic modulation of the agent relative to the other liquid as it is being continuously injected, and based on the dynamic response of the vascular system to the dynamic modulation.

2. The method of claim 1, wherein dynamically modulating the flow rate of the agent being injected includes modulating the injection of the liquid, and wherein characterizing the vascular system includes:
imaging the agent in the vascular system, and
using the imaging to detect differences in modulation characteristics of the agent at a remote portion of the vascular system, relative to modulation characteristics of the injection of the agent at an injection site at which the liquid is dynamically injected into the vascular system.

3. The method of claim 1, wherein
dynamically modulating the flow rate of the agent includes using cardiovascular flow of blood in the vascular system to modulate the concentration of the agent flowing through the system; and
characterizing the vascular system includes detecting changes in the concentration of the agent at a remote portion of the vascular system, relative to a portion of the vascular system at which the liquid is injected.

4. The method of claim 1, wherein dynamically modulating the flow rate of the agent includes modulating the concentration of the agent in the liquid by independently modulating the flow rate of the agent relative to modulation of the flow rate of the other liquid.

5. The method of claim 1, wherein dynamically modulating the flow rate of the agent includes modulating the flow rate of the liquid including the agent.

6. The method of claim 1, wherein dynamically modulating the flow rate of the agent includes modulating the flow rate of the agent between high and low values respectively above and below an offset value while injecting the agent into the vascular system.

7. The method of claim 1, wherein dynamically modulating the flow rate of the agent includes pseudoperiodically or periodically modifying the injection flow rate of the agent to introduce temporal variations in the rate at which the agent is injected into the vascular system, and wherein characterizing the vascular system based on a response of the vascular system to the dynamic modulation includes characterizing the vascular system based on dynamic changes in the response of the vascular system relative to the temporal variations.

8. The method of claim 1, wherein dynamically modulating the flow rate of the agent includes modulating the flow rate of the agent using a waveform selected from the group consisting of: a sinusoidal waveform, a swept sinusoidal waveform, a triangle waveform, a square waveform, and a combination thereof.

9. The method of claim 1, wherein dynamically modulating the flow rate of the agent in the liquid includes modifying a frequency at which the flow rate in the liquid is modified over time.

10. The method of claim 1, wherein dynamically modulating the flow rate of the agent in the liquid includes generating contrast flows based on the cardiac cycle of the vascular system, therein facilitating ECG gating in which a phase relationship of modulation of the agent is synchronized with the cardiac cycle.

11. The method of claim 1, wherein dynamically modulating the flow rate of the agent includes modifying an amplitude at which the flow rate is modified over time, by changing maximum and minimum flow rate values.

12. The method of claim 1, wherein characterizing the vascular system based on a response of the vascular system to the dynamic modulation includes detecting pressure variations in the vascular system, based on the dynamic modulation.

13. The method of claim 1, wherein dynamically modifying the flow rate includes modifying a frequency at which the flow rate of the agent is varied by sweeping over a range of frequencies.

14. The method of claim 1, wherein
dynamically modulating the flow rate of the agent includes, using cardiovascular flow of blood in the vascular system as a carrier signal, coding data onto the cardiovascular flow by modulating one or more of frequency, phase and amplitude characteristics of the concentration of the agent injected via the liquid as the concentration is dynamically modulated; and
characterizing the vascular system includes detecting changes in the data coded onto the cardiovascular flow as the blood flows through the vascular system.

15. An apparatus comprising:
an injector configured and arranged to continuously inject a liquid including an agent and another liquid into a vascular system; and
an actuation controller, including circuitry, configured and arranged to cause the vascular system to exhibit a dynamic response by controlling the injector for dynamically modulating a flow rate of the agent within the liquid being continuously injected into the vascular system over a range of flow rates and prior to the liquid being injected, therein causing the vascular system to exhibit a dynamic response to the dynamic modulation of the flow rate and providing characterization of the vascular system based on a time-varying characteristic of the dynamic modulation and the response of the vascular system to the dynamic modulation.

16. The apparatus of claim 15, wherein the injector includes a dual barrel injector, each barrel having a plunger that is independently controlled by the actuation controller, relative to the plunger in the other barrel.

17. The apparatus of claim 16, wherein the actuation controller includes circuitry programmed to modulate the actuation of each plunger to dynamically modulate the flow rate of the agent as it is injected into the vascular system.

18. The apparatus of claim 15, wherein the actuation controller is configured and arranged to control the injector for dynamically modulating the flow rate by modulating one or both of the concentration and volume of the agent being injected between high and low values respectively above and below an offset value and in accordance with a waveform, while injecting the liquid into the vascular system.

19. The apparatus of claim 15, wherein the actuation controller is configured and arranged to dynamically modulate the flow rate based on an ECG signal from the vascular system.

20. The apparatus of claim 15, further including imaging circuitry configured and arranged to image the agent in the vascular system, the images providing an indication the effect of the vascular system upon the dynamic modulation and therein characterizing the vascular system.

\* \* \* \* \*